United States Patent [19]

Ho et al.

[11] Patent Number: 5,780,431
[45] Date of Patent: Jul. 14, 1998

[54] PHARMACEUTICAL FORMULATIONS OF CORTICOTROPIN RELEASING FACTOR HAVING IMPROVED STABILITY IN LIQUID FORM

[75] Inventors: Bert Ho, Lafayette; Behzad Khosrovi, El Cerrito; Pamela G. Hirtzer, Piedmont, all of Calif.

[73] Assignee: Neurobiological Technologies, Inc., Richmond, Calif.

[21] Appl. No.: 717,306

[22] Filed: Sep. 20, 1996

[51] Int. Cl.$^6$ .................... A61K 38/35; A61K 38/00; A61K 38/22; C07K 14/575
[52] U.S. Cl. ............................ 514/12; 530/324
[58] Field of Search ............... 514/12; 530/324

[56] References Cited

U.S. PATENT DOCUMENTS 5,177,060  1/1993  Wei ............................ 514/15
5,236,901  8/1993  Burks et al. ................. 514/21

OTHER PUBLICATIONS

Lee, S., et al. "Effect of Exposure to an Alcohol Diet for 10 Days on the Ability of Interleukin–1β to Release ACTH and Corticosterone in the Adult Ovariectomized Female Rat", *Alcohol Clin Exp Res.*, vol. 17, No. 5, 1993: pp. 1009–1013.

DeCherney, G.S., et al., "Diurnal Variation in the Response of Plasma Adrenocorticotropin and Cortisol in Intravenous Ovine Corticotropin–Releasing Hormone", *Journal of Clinical Endocrinology and Metabolism*, vol. 61, No. 2, 1985: pp. 273–279.

DeCherney, G.S., et al. "Effect of Ovine Corticotropin–Releasing Hormone Administered During Insulin–Induced Hypoglycemia on Plasma Adrenocorticotropin and Cortisol", *Journal of Clinical Endocrinology and Metabolism*, vol. 64, No. 6, 1987:pp. 1211–1217.

Hermus, A.R.M.M., et al., "Differential Effects of Ovine and Human Corticotrophin–Releasing Factor in Human Subjects", *Clinical Endocrinology*, vol. 21, 1984: 589–595.

Holsboer, F., et al. "Efects of Intravenous Corticotropin–Releasing Hormone upon Sleep–Related Growth Hormone Surge and Sleep EEG in Man [1, 2]", *Neuroendocrinology*, vol. 48, 1988: pp. 32–38.

Koide, Y., et al. "Responsiveness of Hypophyseal–Adrenocortical Axis to Repetitive Administration of Synthetic Ovine Corticotropin–Releasing Hormone in Patients with Isolated Adrenocorticotropin Deficiency", *Journal of Clinical Endocrinology and Metabolism*, vol. 63, No. 2, 1986: pp. 329–334.

Orth, D.N., et al. "Pituitary Microadenomas Causing Cushing's Disease Respond to Corticotropin–Releasing Factor", *Journal of Clinical Endocrinology and Metabolism*, vol. 55, No. 5, 1982: pp. 1017–1019.

Oldfield, E.H., et al. "Corticotropin–Releasing Hormone (CRH) Stimulation in Nelson's Syndrome: Response of Adrenocorticotropin Secretion to Pulse Injection and Continuous Infusion of CRH", *Journal of Clinical Endocrinology and Metabolism*, vol. 62, No. 5, 1986: pp. 1020–1025.

Saphier, P.W., et al. "Comparison of the Clearance of Ovine and Human Corticotrophin–Releasing Hormone (CRH) in man and sheep: a possible role for CRH–binding protein", *Journal of Endocrinology*, vol. 133, 1992: pp. 487–495.

DeBold, C.R., et al. "Effect of Subcutaneous and Intranasal Administration of Ovine Corticotropin–Releasing Hormone in Man: Comparison with Intravenous Administration", *Journal of Clinical Endocrinology and Metabolism*, vol. 60, No. 5, 1985: pp. 836–840.

Schulte, H.M., et al. "Continuous Administration of Synthetic Ovine Corticotropin–Releasing Factor in Man," *The Journal of Clinical Investigation*, vol. 75, 1985: pp. 1781–1785.

Watson, S.J., et al. "Effects of Low Dose Ovine Corticotropin–Releasing Hormone in Humans: Endocrine Relationships and β–Endorphin/β–Lipotropin Responses," *Journal of Clinical Endocrinology and Metabolism*, vol. 66, No. 1, 1988: pp. 10–15.

Stalla, G.K., et al. "Intravenous Application of Ovine and Human Corticotropin Releasing Factor (CRF):ACTH, Cortisol and CRF Levels[1]," *Neuroendocrinology*, vol. 42, 1986: pp. 1–5.

Hermus, A.R.M.M. et al., "Hypotensive Effects of Ovine and Human Corticotrophin–Releasing Factors in Man", *Eur J Clin Pharmacol.*, vol. 31: 1987: pp. 531–534.

Schürmeyer, T.H., et al. "Human Corticotropin–Releasing Factor in Man: Pharmacokinetic Properties and Dose–Response of Plasma Adrenocorticotropin and Cortisol Secretion," *Journal of Clinical Endocrinology and Metabolism*, vol. 59, No. 6, 1984: pp. 1103–1108.

Product Brochure for "Corticobiss (hCRH): The Physiological Releasing–Hormone for the Diagnosis of the Corticotropic Function of the Pituitary Gland," Pharma Bissendorf Peptide: Hannover, Germany: pp. 1–36 (1992).

Schulte, H.M., "Corticotropin–Releasing Factor: Pharmacokinetics in Man," *Journal of Clinical Endocrinology and Metabilism*, vol. 58, 1984: pp. 192–195.

*Primary Examiner*—Cecilia J. Tsang
*Assistant Examiner*—P. Lynn Touzeau
*Attorney, Agent, or Firm*—Flehr Hohbach Test Albritton and Herbert LLP; David J. Brezner; Mark T. Kresnak

[57] ABSTRACT

The present invention relates to novel formulations of corticotropin releasing factor (CRF) having improved stability during storage over extended periods of time as liquids, which retain significant pharmaceutical activity during such storage and/or which are physiologically compatible. The formulations of the present invention comprise (a) a pharmaceutically effective concentration of CRF, (b) a buffer to maintain the pH of the formulation between about 2.0 to about 5.0 or about 6.0 to about 9.0 when in liquid form and (c) an alcohol such as mannitol, sorbitol, methanol, glycerol, or the like. Other aspects of the present invention involve addition of various other components to the formulations described herein for the purpose of decreasing the rate of degradation of the CRF peptide or increasing its solubility in solution. Finally, the present invention is further directed to methods for preparing such novel pharmaceutical formulations of CRF and methods of using those formulations to reduce inflammation and edema in mammals.

39 Claims, 4 Drawing Sheets

```
Human/Rat CRF    SEEPPISLDLTFHLLREVLEMARAEQLAQQAHSNRKLMEII
Ovine CRF        SQEPPISLDLTFHLLREVLEMTKADQLAQQAHSNRKLLDIA
```

PHARMACEUTICAL FORMULATIONS OF CORTICOTROPIN RELEASING FACTOR HAVING IMPROVED STABILITY IN LIQUID FORM

FIELD OF THE INVENTION

The present invention relates to novel formulations of corticotropin releasing factor (CRF) having improved stability during storage over extended periods of time in liquid form, which retain significant pharmaceutical activity during such storage and/or which are pharmaceutically acceptable. The present invention is further directed to methods for preparing such novel pharmaceutical formulations.

BACKGROUND OF THE INVENTION

Corticotropin-Releasing Factor (CRF) is an endogenous 41 amino acid peptide first identified in 1981 as the major hypothalamic hormone responsible for stimulation of the pituitary-adrenal axis. (Vale, W., et al., Science 213:1394–1397 (1981)). More recently, CRF has been shown to have a peripheral, non-endocrine function mediated biological activity as a potent inhibitor of edema and inflammation. (Wei, E. T. et al., Ciba Foundation Symposium 172:258–276 (1993)). This has been confirmed in a series of experiments in which systemic administration of CRF has been shown to inhibit vascular leakage of plasma constituents and associated tissue swelling in response to injury or inflammatory mediators. (Wei, E. T. et al., European J. of Pharm. 140:63–67 (1987), Serda, S. M. et al., Pharm. Res. 26:85–91 (1992) and Wei, E. T. et al., Regulatory Peptides 33:93–104 (1991)). CRF is also known in the art as corticotrop(h)in-releasing hormone (CRH), corticoliberin, corticorelin and CRF-41.

The CRF neuropeptide was first isolated from extracts of ovine hypothalami (OCRF; Vale, W., et al., Science 213:1394–1397 (1981)) and has subsequently been identified and isolated from the hypothalamus of numerous other mammals including rat (rCRF; Rivier, J., et al., Proc. Natl. Acad. Sci. USA 80:4851–4855 (1983)), porcine (PCRF; Schally, A., et al., Proc. Natl. Acad. Sci. USA 78:5197–5201 (1981) and human (hCRF; Shibahara, S., et al., EMBO J. 2:775–779 (1983)). Comparison of the amino acid sequences of CRF peptides from ovine, rat and human has shown that the rat and human peptides are identical, both differing at seven amino acid positions from the ovine peptide, the differences occurring largely in the C-terminal region of the peptides (Hermus, A., et al., J. Clin. Endocrin. and Metabolism 58:187–191 (1984) and Saphier, P., et al., J. Endocrin. 133:487–495 (1993)).

CRF has been shown to be a safe and useful pharmaceutical agent for a variety of different applications in humans. Specifically, in vivo administration of CRF has been extensively employed to help elucidate the cause of hyper- and hypo-cortisolemic conditions in humans and is an extremely useful diagnostic and investigative tool for various other disorders affecting the hypothalamic-pituitary-adrenal axis, including endogenous depression and Cushing's disease (Chrousos, G., et al., N. Eng. J. Med. 310:622 (1984) and Lytras, N., et al., Clin. Endocrinol. 20:71 (1984)). In fact, in vivo administration of CRF is useful to test corticotropic function of the anterior pituitary in all cases in which an impairment of the anterior pituitary function is suspected. This applies to patients with pituitary tumors or craniopharyngiomas, patients with suspected pituitary insufficiency, panhypopituitarism or empty sella syndrome, as well as patients with traumatic or post-operative injury to the pituitary region and patients who have undergone radiotherapy of the pituitary region. Thus, CRF clearly has utility for diagnostic analysis of the hypothalamus-pituitary-adrenal (HPA) axis.

For important peripheral applications, CRF also possesses in vivo anti-inflammatory activity. With regard to the anti-inflammatory activity of the CRF peptide, CRF prevents vascular leakage induced by a variety of inflammatory mediators that appear to act selectively on post-capillary venules in skin. CRF also inhibits injury- and inflammatory mediator-induced leakage from capillaries in muscle, cerebral micro-vessels, and lung alveolar capillaries. These observations suggest that CRF acts throughout the microcirculation to preserve or restore endothelial cell integrity, thereby inhibiting fluid egress and white blood cell trafficking from the intravascular space and accumulation at sites of injury.

In light of the novel anti-inflammatory activity of the CRF peptide, numerous clinical indications are evident. For example, clinical indications for which the CRF peptide may find use include rheumatoid arthritis, edema secondary to brain tumors or irradiation for cancer, edema resulting from stroke, head trauma or spinal cord injury, post-surgical edema, asthma and other respiratory diseases and cystoid macular edema of the eye.

For use in the above described in vivo applications, CRF may be administered to subjects by a variety of means including subcutaneously, intravenously, intramuscularly or nasally as an aerosol. Such varying means of administration usually require the preparation of numerous different CRF formulations. Generally, however, CRF peptide formulations that are used for in vivo administration are synthesized and stored as a solid lyophilized powder which is reconstituted into a pharmaceutically acceptable liquid immediately prior to use. Such formulations are usually preferred because it is recognized by those skilled in the art that lyophilized preparations generally maintain pharmaceutical activity better over time than their liquid counterparts. However, lyophilized formulations are disadvantageous in that they require reconstitution immediately prior to use and are, therefore, more difficult to use in a clinical or outpatient setting. Furthermore, lyophilized formulations are generally more difficult and expensive to manufacture because they require the extra step of lyophilization during their preparation.

Various experimental preparations of the CRF peptide, whether reconstituted from previously lyophilized material or not, have been employed for administration to both humans and animals. For example, illustrative preparations of CRF include 0.0001N HCl–154mM NaCl, 0.1% lactose, 0.25% human serum albumin (HSA), 0.5 mM ascorbic acid and 0.9% benzyl alcohol (DeCherney, G., et al. J. Clin. Endocrin. and Metabolism 61:273–279 (1985) and DeCherney, G., et al., J. Clin. Endocrin. and Metabolism 64:1211–1217 (1987)), pH 2.0 saline (Hermus, A., et al., Clin. Endocrin. 21:589–595 (1984) and Hermus, A., et al. Eur. J. Clin. Pharmacol. 31:531–534 (1987)), 0.02% HCl and 10% albumin in 0.9% saline (Holsboer, F., et al., Neuroendocrinology 48:32–38 (1988)), 0.05M acetic acid and 5% mannitol (Koide, Y., et al., J. Clin. Endocrin. and Metabolism 63:329–335 (1986)), 0.04M phosphate buffer (pH 7.3) containing 0.1% BSA and 0.01% ascorbic acid (Lee, S., et al., Alcohol. Clin. Exp. Res. 17:1009–1013 (1993)), 0.001N HCl–154 mM NaCl, 0.9% benzyl alcohol, 10% mannitol and 0.25% HSA (Orth, D., et al., J. Clin. Endocrin. and Metabolism 55:1017–1019 (1982)) and sterile water plus 5% mannitol (Schulte, H., et al., J. Clin.

*Endocrin. and Metabolism* 58:192–196 (1984) and Schurmeyer, T., et al., *J. Clin. Endocrin. and Metabolism* 59:1103–1108 (1984)).

The above described CRF formulations, however, are inappropriate for large scale commercial pharmaceutical use for a variety of reasons. For example, many of the above described formulations may result in significant irritation if administered subcutaneously or nasally due to their chemical formulations, pH, and the like. Moreover, many of the above described formulations, if not lyophilized and reconstituted immediately prior to use, fail to account for the fact that the CRF peptide is highly susceptible to degradation and concomitant loss of pharmaceutical activity if stored for extended periods of time in the presence of certain additives and at certain pH's. Furthermore, CRF is relatively insoluble at certain pH's, specifically at pH's in the range of about 5–6. As described above, in attempts to avoid significant degradation during storage, many of the above described formulations are actually prepared as lyophilized material which is reconstituted as a physiologically compatible liquid immediately prior to use.

Thus, there is substantial interest in being able to provide for improved pharmaceutical formulations of CRF which have adequate solubility and which are stable during storage over extended periods of time. It is, therefore, an object of the present invention to prepare pharmaceutical formulations of CRF which can be stored in liquid form over extended periods of time without appreciable degradation of the peptide or significant loss of pharmaceutical efficacy. Such liquid formulations obviate the need for lyophilization and subsequent reconstitution of the peptide before use, thus permitting more convenient administration. In developing such liquid formulations, one must take into account the mode of administration of the formulation, the solubility of the CRF peptide in that liquid formulation, the stability of the peptide over extended periods of storage as a liquid at varying pH's, temperatures, etc.

It is a further object of the present invention to prepare formulations of CRF which are pharmaceutically acceptable, meaning that they do not result in significant irritation to the subject when administered, particularly by the subcutaneous and nasal routes.

A still further object of the present invention is to provide methods for preparing the novel pharmaceutical formulations of the present invention and using such formulations for reducing inflammation and edema in mammals.

Other objects, features and characteristics of the present invention will become more apparent upon consideration of the following description and the appended claims.

The publications and other materials cited herein are used to illuminate the background of the invention and to provide additional details with regard to its practice. Each of the publications referenced herein are hereby expressly incorporated by reference in their entirety.

SUMMARY OF THE INVENTION

The present invention is predicated upon the identification and preparation of novel formulations of CRF having acceptable solubility and which are stable when stored as liquids for extended periods of time, which do not lose significant pharmaceutical activity during such storage and/ or which are pharmaceutically acceptable in that they are well tolerated in terms of irritation when administered. Thus, one aspect of the present invention relates to pharmaceutically acceptable formulations of CRF comprising (a) a pharmaceutically effective amount of CRF, (b) a buffer at a concentration of from about 1 mM to about 50 mM which functions to maintain the pH of said formulation between about 2.0 to about 5.0 or between about 6.0 to about 9.0 when in liquid form, wherein the anion of said buffer is selected from the group consisting of acetate, phosphate, carbonate, succinate, citrate, borate, tartrate, fumarate and lactate and (c) an alcohol, in a concentration of from about 1% to about 10%, wherein said alcohol is selected from the group consisting of mannitol, sorbitol, ribotol, arabitol, xylitol, inositol, galactitol, methanol, ethanol and glycerol.

In other aspects of the present invention, various components are optionally included in the formulation as described above and may replace the buffer. Such additives include amino acids such as methionine, arginine, lysine, glutamic acid, cysteine, glutathione, and the like. Amino acids are generally present in concentrations ranging from about 1 mM to about 100 mM.

In yet other aspects of the present invention, various sugars are optionally included in the CRF formulations as described above. Such sugars include, for example, glucose, sucrose, lactose, fructose, trehalose, mannose, and the like. Additive sugars are generally present in concentrations ranging from about 1% to about 10%.

In still other aspects of the present invention, potential stabilizing compounds such as ferric, cupric, magnesium and zinc salts, and the like, may be added to the formulations described above. These potential stabilizers may provide a protective effect against degradation of the CRF peptide and, generally, are present in concentrations ranging from about 0.05 mM to about 1 mM.

In yet other aspects of the present invention, antioxidants such as butylated hydroxytoluene (BHT), and the like or chemically compatible preservatives such as benzyl alcohol, chlorobutanol, phenol, cresol, methyl paraben, propyl paraben, and the like may also be added to the formulations described above. Such compounds may also provide a protective effect against degradation of the CRF peptide in solution and inhibit the growth of contaminating substances, respectively.

Other aspects of the present invention are directed to methods for preparing the novel pharmaceutical formulations of the present invention and methods for enhancing the stability of CRF in a formulation thereof by adding varying concentrations of amino acids, thereby reducing the rate of degradation of the CRF peptide.

Another aspect of the present invention relates to methods for reducing inflammation and edema in mammals comprising administering a therapeutically effective amount of the novel CRF formulation(s) of the present invention.

Other aspects will be readily apparent to those of ordinary skill in the art.

DETAILED DESCRIPTION OF THE INVENTION

The present invention is based upon the identification and preparation of novel formulations of CRF which are stable when stored as liquids for extended periods of time, which do not lose significant pharmaceutical activity during such storage and/or which are pharmaceutically acceptable in that they are well tolerated in terms of irritation when administered. The present invention is also directed to methods for preparing such formulations, methods for enhancing the stability of the CRF peptide in such formulations and methods of using such formulations for reducing inflammation and edema in mammals.

Figure 1:
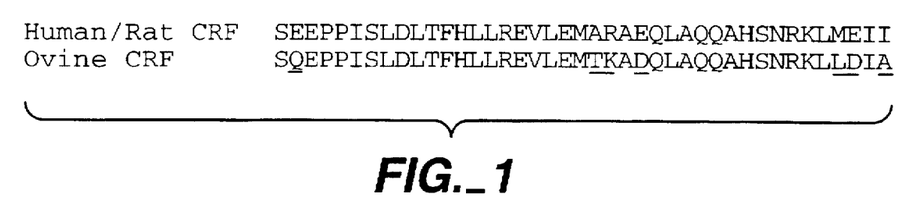
FIG. 1 shows the amino acid sequences of the human and rat CRF peptides as compared to that of the ovine CRF peptide. Amino acids are presented as their standard one-letter designations. Amino acids in the ovine sequence which are presented in bold font and are underlined are those that differ from the human/rat CRF sequence.

As used herein, the terms "corticotropin releasing factor", "CRF", "corticotrop(h)in-releasing hormone", "CRH", "corticoliberin", "corticorelin", "CRF-41" or grammatical equivalents thereof have a functional definition and refer to peptides which share one or more of the biological activities of the native, intact CRF peptide. Such biological activities include, for example, the ability to stimulate the release of ACTH, the ability to inhibit edema in vivo and the ability to bind to CRF receptors. Each of the above terms is intended to denote the 41 amino acid human, rat, ovine, sheep, goat, porcine and fish corticotropin releasing factor peptides and CRF peptides from other mammals, whether isolated from natural source extraction and purification, from recombinant cell culture systems or synthesized using peptide synthesis technology. These terms are also intended to denote other CRF-related peptides which share one or more of the biological activities of the native CRF peptides such as urocortin (Vaughan, J., et al., *Nature* 378:287–292 (1995), Donaldson, C. J., et al., *Endocrinology* 137(5):2167–2170 (1996) and Turnbull, A. V., et al., *Eur. J. Pharm.* 303:213–216 (1996)), urotensin I (Lederis, K., et al., *Science* 218:162–164 (1982)) and sauvagine (Montecucchi, P. C., et al., *Int. J. Pep. Prot. Res.* 16:191–199 (1980)). The CRF peptides employed in the formulations of the present invention are preferably synthesized using solid- or solution-phase peptide synthesis techniques, however, other sources of the CRF peptide are readily available to the ordinarily skilled artisan. The amino acid sequences of the human, rat and ovine CRF peptides are presented in FIG. 1. The terms "corticotropin releasing factor" and "CRF" likewise cover biologically active CRF equivalents; e.g., peptides differing in one or more amino acids in the overall amino acid sequence as well as substitutional, deletional, insertional and modified amino acid variants of CRF which substantially retain the biological activity normally associated with the intact CRF peptide.

The term "pharmaceutically acceptable" when used in reference to the formulations of the present invention denotes that a formulation does not result in an unacceptable level of irritation in the subject to whom the formulation is administered by any known administration regimen. What constitutes an unacceptable level of irritation will be readily determinable by those of ordinary skill in the art and will take into account erythema and eschar formation as well as the degree of edema associated with administration of the formulation.

The novel formulations of the present invention comprise, in part, a therapeutically effective amount of the CRF peptide. By "therapeutically effective amount" is meant that the formulation contains a concentration of CRF which, when administered to an individual in need of such administration by standard administration regimens, results in a desired pharmacological or therapeutic effect. Generally, a therapeutically effective amount of CRF in a formulation ranges from about 0.1 mg/ml to 10 mg/ml. Preferably, a therapeutically effective amount of CRF ranges from about 0.5 mg/ml to about 5 mg/ml and more preferably from about 0.5 mg/ml to about 3 mg/ml.

The novel formulations of the present invention further comprise, in part, a buffer. Buffers contemplated herein include buffers having as their anionic entity acetate, phosphate, carbonate, succinate, citrate, borate, tartrate, fumarate, lactate, and the like. To retain approximate electrical neutrality, the negatively charged anionic species may be balanced by the presence of an approximately equal amount of a positively charged counterion. Counterions which find use herein are those which are physiologically acceptable and include sodium (Na), potassium (K), calcium (Ca), ammonium (NH$_4$), and the like. Such anionic buffers, however, may be replaced entirely by amino acids such as methionine, arginine, lysine, glutamic acid, cysteine, glutathione and the like. Although such amino acids are weak buffers, they do provide adequate buffering capacity for the formulations of the present invention.

Buffers employed in the novel formulations of the present invention are physiologically acceptable and generally range in concentration from about 1 mM to about 50 mM. Preferably, however, the buffer employed ranges in concentration from about 5 mM to about 30 mM and more preferably from about 5mM to about 20 mM. Additionally, it is preferred that the buffer employed possesses a relatively low ionic strength, however, high ionic strength buffers may also find use.

It is also known that various buffers may be volatilized to certain extents when subjected to the process of lyophilization. As such, non-volatile buffers are preferred when the CRF-containing formulation is to be lyophilized. Examples of non-volatile buffers which find use include those which have anionic entities such as succinate, tartrate, phosphate, and the like.

The function of the buffer in the novel formulations of the present invention is, in part, to maintain an approximately constant pH of the formulation when in liquid form. Generally, pH's in the range of about 2.0 to about 5.0 or about 6.0 to about 9.0 can be employed, however, it is preferred that the pH of the liquid formulation range from about 3.0 to about 4.5 or about 6.5 to about 8.0. More preferably, the pH of the liquid formulations of the present invention range from about 3.8 to about 4.2 or about 7.0 to about 7.5. Most preferably, acidic pH's are employed. Virtually any organic or inorganic acid can be employed to lower the pH of a liquid formulation of the present invention provided that said acid does not have a significant detrimental effect on the stability or the solubility of the CRF peptide in solution. Illustrative examples of acids which may find use include HCl, $H_3PO_4$, $H_2SO_4$, acetic acid, and the like.

It has also been determined herein that addition of an alcohol or sugar alcohol to a pharmaceutical formulation of the CRF peptide has a beneficial effect on stability of the peptide during storage over an extended period of time and on the potential for irritation when the formulation is administered to an individual. As such, the novel formulations of the present invention further comprise, in part, an alcohol. Alcohols which find use in the formulations of the present invention include mannitol, sorbitol, ribotol, arabitol, xylitol, inositol, galactitol, methanol, ethanol, glycerol, and the like. Generally, the concentration of alcohol employed in the novel formulations of the present invention ranges from about 1% to about 10%, preferably from about 3% to about 7.5% and more preferably from about 4% to about 6%.

Preferably, the CRF-containing formulations of the present invention possess an osmolarity which is approximately physiological, however, those having non-physiological osmolarities may also find use. By "physiological osmolarity" is meant that the osmolarity of the formulation is that normally found at the physiological site of administration. It is also known that the amount and type of alcohol or sugar alcohol added to the formulation affects the osmolarity of that formulation and, thus, the amount and type of additive alcohol can be chosen so as to bring the osmolarity of the formulation into appropriate physiological ranges. Osmolarity may also be affected by the addition to the formulation of physiologically compatible salts and, therefore, the addition of virtually any physiologically compatible salt is contemplated for use in altering osmolarity of the CRF-containing formulation. Salts which find use are those which are physiologically compatible and which do not have a substantially detractive effect on CRF stability or solubility.

The formulations of the present invention may also optionally include other components in amounts preferably not detracting from the preparation of active, stable CRF peptide formulations and in amounts suitable for effective, safe pharmaceutical administration.

Generally, the primary route of degradation of the CRF peptide in solution is through oxidation of methionine residues present in the peptide. Other sources of degradation include peptide bond hydrolysis and deamidation. We have determined that the addition of free amino acids to the formulations of the present invention functions to enhance the stability of the CRF peptide. The addition of free methionine enhances the stability of CRF by providing additional available sites for oxidation events that occur in the system. The presence of these additional available sites for oxidation, therefore, most likely effectively reduces the number of oxidation events occurring on the CRF peptide itself and, thus, enhances the stability of the peptide in solution.

As such, in one embodiment of the present invention, free amino acids are added, either singly or in combination, to the formulations described herein to enhance the stability of the CRF peptide in those formulations. Amino acids which find use include methionine, arginine, lysine, glutamic acid, cysteine, glutathione and the like. Generally, free amino acids are added in a concentration ranging from about 1 mM to about 100 mM each, preferably from about 5 mM to about 80 mM each and more preferably from about 20 mM to about 50 mM each. Such amino acids may be in addition to, or may replace, the anionic buffer in the formulations of the present invention.

In another embodiment, various sugars, both reducing and non-reducing, may be added to the liquid formulations of the present invention. As such, as used herein, the term "sugars" refers to both reducing and non-reducing sugars including, for example, glucose, sucrose, lactose, fructose, trehalose, mannose, and the like. Generally, sugars are present in the formulations of the present invention at a concentration of about 1% to about 10%, preferably from about 3% to about 7.5% and more preferably from about 4% to about 6%.

In yet another embodiment, potential stabilizing compounds are added to the formulations of the present invention to further provide a stabilizing effect on the CRF peptide. Compounds which find use include ferric, magnesium, cupric and zinc salts, and the like. Preferably, compounds such as ferric, magnesium, cupric and zinc salts are added to the formulations of the present invention in a concentration ranging from about 0.05 mM to about 5.0 mM, more preferably from about 0.1 mM to about 1.0 mM.

Additionally, the novel formulations of the present invention may optionally include antioxidant compounds such as butylated hydroxytoluene (BHT), and the like. Generally, antioxidant compounds are employed in concentrations ranging from about 0.01 mM to about 5.0 mM and preferably from about 0.05 mM to about 2.0 mM.

The novel formulations of the present invention may also optionally include chemically compatible preservatives in effective concentrations which are known in the art. By "chemically compatible" is meant that the preservative does not significantly increase the rate of degradation of the CRF peptide when present in a liquid or lyophilized formulation. Illustrative examples of chemically compatible preservatives which find use in the presently described liquid formulations include benzyl alcohol, chlorobutanol, phenol, cresol, methyl paraben, propyl paraben, and the like.

Additionally, the improved formulations of the present invention may optionally include one or more non-ionic detergents, such as polysorbate 20, polysorbate 80, and the like, in amounts of about 0.001% to about 1%, in order to further enhance the activity stability of the CRF peptide. In addition, other pharmaceutically acceptable excipients well known to those of ordinary skill in the art may also form part of the formulations of the present invention. These can include, for example, chelating agents, such as disodium edetate (EDTA) and various other cosolvent components, such as polyethylene glycol (PEG).

The formulations of the present invention can exist either in liquid or solid form. Preferably, the formulation is in liquid form to allow for ease of administration in a clinical setting. However, when in a solid form, it is preferred that the formulation be lyophilized.

The formulations of the present invention are prepared in general by combining the components of the formulation by using generally available pharmaceutical combining techniques, known per se.

The formulations of the present invention are stable when stored at about 2° C.–8° C. for extended periods of time. By "stable" is meant that the CRF peptide is less than 20% degraded when stored at 2° C.–8° C. for 24 months and less than 10% degraded when stored at 2° C.–8° C. for 12 months. The percent degradation of the CRF peptide is determined by submitting the formulation to HPLC analysis and dividing the area under the peak corresponding to the CRF peptide by the total area under all detectable peaks. Preferably, the CRF peptide of the formulation is less than 10% degraded when stored at 2° C.–8° C for 24 months and less than 5% degraded when stored at 2° C.–8° C for 12 months and more preferably less than 5% degraded when stored at 2° C.–8° C for 24 months.

The following examples are provided merely to illustrate various embodiments of the present invention and are not intended to be limiting of the subject matter disclosed herein.

Experimental

EXAMPLE 1

Synthesis of CRF Peptides

CRF peptides can be synthesized using well known Merrifield solid phase peptide synthesis technology. Specifically, the first carboxy-terminus amino acid of the CRF peptide sequence is attached to an insoluble polystyrene (benzhydrylamine derivative) resin by an amine bond and the remaining amino acids of the peptide are subsequently linked in sequence. The amino acid residues are chemically protected to protect against undesirable coupling reactions between reactive side chains of the amino acid subunits. Once synthesis of the peptide is complete, liquid hydrogen fluoride is used to cleave the peptide from the resin and to deprotect the previously protected reactive sites on the amino acid subunits.

Once completely synthesized, the crude CRF peptide is then purified by reverse-phase chromatography using a C-18 resin and an acetic acid/acetonitrile buffer system. Purer fractions are pooled for further purification using C-18 semi-preparative chromatography. Elution from this column uses an acetic acid/acetonitrile and/or an ammonium bicarbonate/acetonitrile buffer system. The purest fractions are pooled and lyophilized. The purified peptide is then stored in glass containers at –25° C. to –15° C. until ready for the preparation of a liquid formulation thereof.

EXAMPLE 2

Preparation of Liquid Formulations of CRF from Synthesized Peptide

From the solid CRF peptide synthesized in Example 1 above, a pH 4.0 liquid formulation of 1 mg/ml CRF in 20 mM acetate buffer and 5% mannitol was prepared as follows. Solid CRF peptide is removed from freezer storage and is allowed to equilibrate at room temperature for at least 30 minutes. While the CRF peptide is equilibrating, 1,100 ml of sterile water and 1.36 ml glacial acetic acid is added to a sterile 2-liter flask and the solution is mixed for a minimum of 5 minutes. The solution is then brought up to 1,200 ml with sterile water and mixed for at least an additional 5 minutes. This forms the "acetic acid" solution.

While the acetic acid solution is mixing, 1.088 grams of sodium acetate trihydrate is dissolved in 300 ml of sterile water, the solution is brought up to 400 ml with sterile water and is mixed for at least 5 minutes. This forms the "sodium acetate" solution. Then, in a sterile 2-liter flask, 1,100 ml of the acetic acid solution and 240 ml of the sodium acetate solution are combined, mixed for a minimum of 5 minutes and the pH is then adjusted to 4.0 using the remaining acetic acid solution to lower the pH or the remaining sodium acetate solution to raise the pH. This solution is then sparged with filtered nitrogen for at least 30 minutes. This forms the "buffer" solution.

Once sparged with nitrogen for at least 30 minutes, 800 ml of the buffer solution is transferred to a 2-liter graduated cylinder and 55 grams of mannitol is added. This solution is then mixed for at least 10 minutes until the mannitol is completely dissolved and while continuing to sparge the solution with nitrogen. The pH of this solution is then adjusted to 4.0 by adding either the acetic acid solution to lower the pH or the sodium acetate solution to raise the pH. This forms the "buffer/mannitol" solution.

Once the buffer/mannitol solution is adjusted to pH 4.0, 1.1 grams (net peptide weight) of solid CRF is added and the solution is mixed until the CRF is completely dissolved. A nitrogen flush is maintained over the solution during this time. Once the added CRF is completely dissolved, the volume of the solution is brought up to 1,100 ml with buffer/mannitol solution and mixed while maintaining a nitrogen flush over the solution. This forms the "CRF/buffer/mannitol" solution.

The CRF/buffer/mannitol solution is then filtered through a sterile 0.22 micron pore size Durapore membrane filter while a nitrogen flush is maintained over the filtered solution. Sterile storage vials are then flushed with filtered nitrogen and 0.5 ml to 2.0 ml of the CRF/buffer/mannitol solution is aliquofted into vials which are then stoppered, sealed and stored at 2°–8° C. The resulting liquid formulation is 1.0 mg/ml CRF in 20 mM acetate buffer, pH 4.0 and 5% mannitol.

EXAMPLE 3

Solubility of CRF in Various Buffer Solutions

In an effort to develop liquid formulations of CRF useful for commercial pharmaceutical purposes, experiments designed to measure the solubility of CRF in a variety of different buffer solutions were carried out. Specifically, CRF was added in increasing amounts to a variety of different buffer solutions at various different concentrations and pH's, either in the presence or absence of other excipient additives and the solubility of the CRF product was determined. Table 1 summarizes the results of these experiments measuring the solubility of CRF in various phosphate, citrate and acetate buffers, either in the presence or absence of various excipients such as NaCl and mannitol. CRF solubility is expressed in gross weight of CRF in mg/ml of solution.

TABLE 1

Solubility of CRF in Various Buffer Solutions

| pH (mg/ml) | BUFFER | SALT | ALCOHOL | SOLUBILITY |
|---|---|---|---|---|
| 2.0 | 10 mM PO4 | 138 mM NaCl | | 50 |
| 3.6 | 10 mM PO4 | 138 mM NaCl | | 2.64 |
| 4.2 | 10 mM PO4 | 138 mM NaCl | | 0.29 |
| 4.5 | 10 mM PO4 | 138 mM NaCl | | 0.62 |
| 5.6 | 10 mM PO4 | 138 mM NaCl | | 0.31 |
| 6.7 | 10 mM PO4 | 138 mM NaCl | | 0.52 |
| 7.1 | 10 mM PO4 | 138 mM NaCl | | 0.48 |
| 7.1 | 10 mM PO4 | 138 mM NaCl | | 0.84 |
| 6.02 | 5 mM PO4 | | | 0.08 |
| 6.96 | 5 mM PO4 | | | 0.47 |
| 7.7 | 5 mM PO4 | | | 0.46 |
| 7.32 | 20 mM PO4 | | | 1.46 |
| 4.0 | 25 mM Citrate | 150 mM NaCl | | 0.02 |

TABLE 1-continued

Solubility of CRF in Various Buffer Solutions

| pH | BUFFER | SALT | ALCOHOL | SOLUBILITY (mg/ml) |
|---|---|---|---|---|
| 4.0 | 25 mM Citrate | | | 0.04 |
| 5.1 | 25 mM Citrate | 150 mM NaCl | | 0.01 |
| 5.1 | 25 mM Citrate | | | 0.02 |
| 6.1 | 25 mM Citrate | 150 mM NaCl | | 0.07 |
| 6.1 | 25 mM Citrate | | | 0.1 |
| 4.08 | 5 mM Citrate | 150 mM NaCl | | 0.16 |
| 4.08 | 5 mM Citrate | | | 0.2 |
| 4.92 | 5 mM Citrate | 150 mM NaCl | | 0.01 |
| 4.92 | 5 mM Citrate | | | 0.03 |
| 5.84 | 5 mM Citrate | 150 mM NaCl | | 0.02 |
| 5.84 | 5 mM Citrate | | | 0.04 |
| 4.2 | 25 mM HOAc | | | 29 |
| 4.49 | 25 mM HOAc | 150 mM NaCl | | 0.28 |
| 4.49 | 25 mM HOAc | | | 5.34 |
| 4.9 | 25 mM HOAc | 150 mM NaCl | | 0.14 |
| 4.9 | 25 mM HOAc | | | 0.37 |
| 6.24 | 25 mM HOAc | 150 mM NaCl | | 0.05 |
| 6.24 | 25 mM HOAc | | | 0.09 |
| 4.2 | 5 mM HOAC | 150 mM NaCl | | 1.17 |
| 4.4 | 5 mM HOAC | | | 33 |
| 4.6 | 5 mM HOAC | | 5% mannitol | 2.2 |
| 4.7 | 5 mM HOAC | | 1% mannitol | 1.96 |
| 4.72 | 5 mM HOAC | | 1% Tween | 1.97 |
| 4.81 | 5 mM HOAC | | | 1.13 |
| 5.0 | 5 mM HOAC | | | 0.13 |
| 6.0 | 5 mM HOAC | | | 0.03 |
| 4.26 | 20 mM HOAc | | 5% mannitol | 14.5 |
| 4.34 | 20 mM HOAc | | 5% mannitol | 11.2 |
| 4.45 | 20 mM HOAc | | 5% mannitol | 13.8 |
| 4.52 | 20 mM HOAc | | 5% mannitol | 12.5 |
| 4.73 | 20 mM HOAc | | 5% mannitol | 1.53 |
| 4.94 | 20 mM HOAc | | 5% mannitol | 0.07 |
| 5.23 | 20 mM HOAc | | 5% mannitol | 0.04 |

The results presented in Table 1 demonstrate that CRF is very soluble in phosphate buffer between pH 2 and 3.6 and becomes less soluble between pH 5 and 6. The solubility of CRF then appears to increase when the pH is raised to greater than or equal to 7.0.

The results presented in Table 1 further demonstrate that CRF is very insoluble (<0.2 mg/ml) in citrate buffer between pH 4 and 6.

Finally, CRF is very soluble in acetate buffer between pH 4 and 5 without added NaCl whereas addition of 150 mM NaCl acts to significantly reduce CRF solubility in acetate buffer. The addition of 5% mannitol does not appear to detrimentally affect the solubility of CRF at any pH tested.

Next, because it is known that certain buffers may be volatilized when lyophilized, further experiments were conducted as described above to examine the solubility of CRF in various other non-volatile buffer solutions. The results of these experiments are presented in Table 2.

TABLE 2

Solubility of CRF in Various Non-Volatile Buffer Solutions

| Buffer Solution | CRF solubility (net mg/ml) |
|---|---|
| 25 mM Ascorbic, pH 4.0 | 4.5 |
| 25 mM Lactic, pH 4.0 | 1.9 |
| 25 mM Succinic, pH 4.0 | 4.2 |
| 25 mM Tartaric, pH.4.0 | 0.2 |
| 10 mM Phosphate, pH 7.3 | 3.0 |

TABLE 2-continued

Solubility of CRF in Various Non-Volatile Buffer Solutions

| Buffer Solution | CRF solubility (net mg/ml) |
|---|---|
| 10 mM Phosphate, pH 7.3 + 0.25% arginine | 2.0 |
| 10 mM Phosphate, pH 7.3 + 25 mM ascorbate | 1.2 |
| 10 mM Phosphate, pH 7.3 + 0.25% glycine | 2.2 |

The results presented in Table 2 demonstrate that CRF is extremely soluble in the ascorbic, lactic, succinic and phosphate buffers tested. Solubility was significantly reduced in the tartaric buffer tested.

EXAMPLE 4

CRF Stability Studies in Ascorbic-, Succinic- and Phosphate-Based Buffers

Based upon the results presented in Table 2 demonstrating that CRF is very soluble in ascorbic-, succinic- and phosphate-based buffers, formulations having different concentrations of CRF were prepared in each of the three buffers and the rate of degradation of the CRF peptide in those formulations was determined after storage for 5 days at either 4° C. or 30° C. In each formulation, buffer salts were set at 20 mM and mannitol was present at 5%. The rate of degradation was determined by measuring the concentration of CRF in each formulation prior to storage and again after 5 days in storage at each temperature examined. The results of these experiments are presented in Table 3.

TABLE 3

Stability of CRF in Ascorbic-, Succinic- and Phosphate-Based Buffers

| Formulation | Measured CRF Concentration (mg/ml) | | |
|---|---|---|---|
| days | time = 0 | 4° C., 5 days | 30° C., 5 days |
| Ascorbic, pH 4.0 (1 mg/ml CRF) | 0.94 | 0.90 | 0.61 |
| Ascorbic, pH 4.0 (0.5 mg/ml CRF) | 0.56 | 0.52 | 0.35 |
| Ascorbic, pH 4.0 (0.2 mg/ml CRF) | 0.27 | 0.15 | 0.06 |
| Succinic, pH 4.0 (1 mg/ml CRF) | 0.98 | 1.02 | 0.99 |
| Succinic, pH 4.0 (0.5 mg/ml CRF) | 0.49 | 0.49 | 0.51 |
| Succinic, pH 4.0 (0.2 mg/ml CRF) | 0.22 | 0.21 | 0.21 |
| Phosphate, pH 7.4 (1 mg/ml CRF) | 1.00 | 1.01 | 0.97 |
| Phosphate, pH 7.4 (0.5 mg/ml CRF) | 0.42 | 0.41 | 0.41 |
| Phosphate, pH 7.4 (0.2 mg/ml CRF) | 0.16 | 0.15 | 0.15 |

The results presented in Table 3 demonstrate that while the ascorbic-based formulation is detrimental to the stability of CRF at both 4° C. and 30° C., the succinic-based and phosphate-based formulations did not result in any significant degradation of the solubilized CRF peptide.

EXAMPLE 5

Studies Analyzing the Effect of Mannitol and Sorbitol on CRF Stability in Liquid Formulations Experiments were carried out to determine the effect of 5% mannitol or 5% sorbitol on the stability of liquid formulations of CRF during long-term storage at 4° C. or 30° C. Specifically, the following liquid formulations were prepared and analyzed for stability during storage at either 4° C. or 30° C.:

1 mg/ml CRF, pH 4.0 acetate (20 mM)

1 mg/ml CRF, pH 4.0 acetate (20 mM), 5% mannitol 1 mg/ml CRF, pH 4.0 acetate (20 mM), 5% sorbitol 1 mg/ml CRF, pH 4.5 acetate (20 mM)

1 mg/ml CRF, pH 4.5 acetate (20 mM), 5% mannitol 1 mg/ml CRF, pH 4.5 acetate (20 mM), 5% sorbitol Stability of the peptide in each formulation tested was determined by analyzing each of the samples by HPLC at various timepoints and measuring the amount of peptide degradation that had occurred at each timepoint by calculating the area under the peak corresponding to CRF as compared to the total area under all peaks detected.

The results obtained from these experiments demonstrated that after 2-weeks in storage at either 4° C. and 30° C., the pH 4.0 formulations were equally stable as the pH 4.5 formulations and, therefore, the pH 4.5 formulations were dropped from the study.

Figure 2:
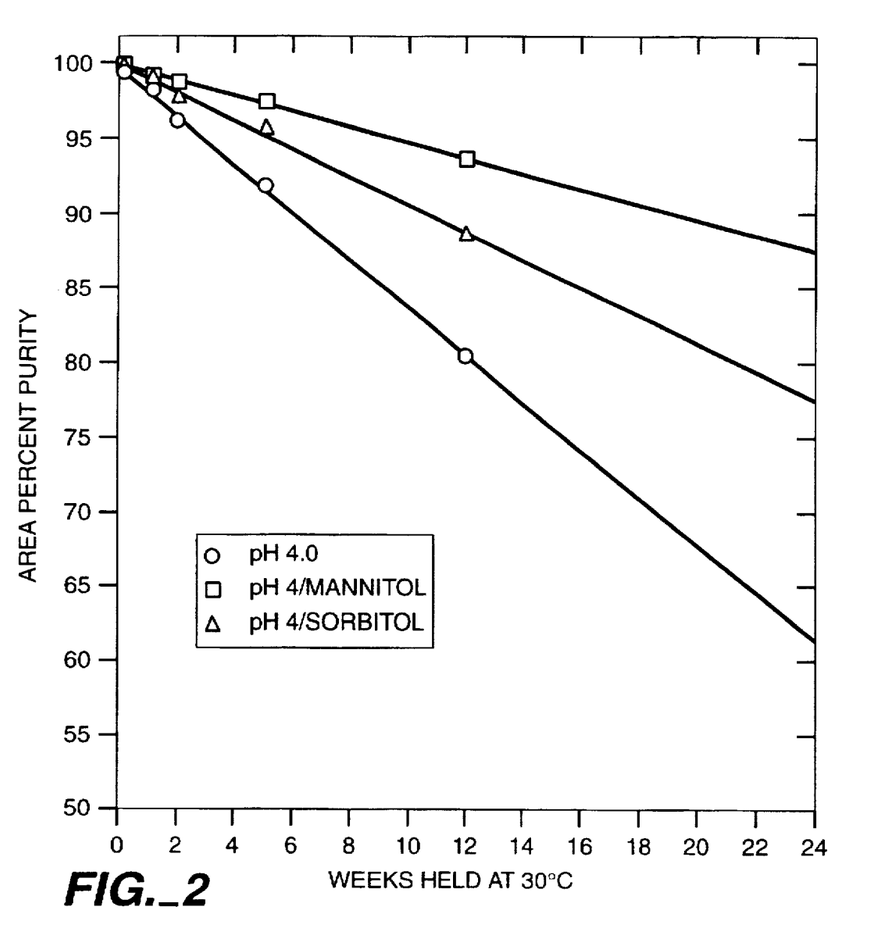
FIG. 2 shows the relative rates of degradation of CRF during storage at 30° C. in liquid formulations wherein the liquid formulations tested are 1 mg/ml CRF, pH 4.0, 20 mM acetate ("pH 4.0"), 1 mg/ml CRF, pH 4.0, 20 mM acetate, 5% mannitol ("pH 4/mannitol") and 1 mg/ml CRF, pH 4.0, 20 mM acetate, 5% sorbitol ("pH 4/sorbitol").

The results of the studies for the pH 4.0 formulations performed at 30° C., are shown in FIG. 2. Specifically, the data presented in FIG. 2 indicate that after 2-weeks of storage at 30° C., the pH 4.0 mannitol-containing formulation showed a slight trend toward greater stability than the sorbitol-containing formulation. Both the mannitol-containing and sorbitol-containing formulations, however, were significantly more stable than the formulation lacking additive alcohol. This same pattern was consistently observed through 12 weeks of storage at 30° C. Thus, these data indicate that the addition of an alcohol such as mannitol or sorbitol functions to provide protection against degradation of CRF when stored as a liquid at 30° C.

Figure 3:
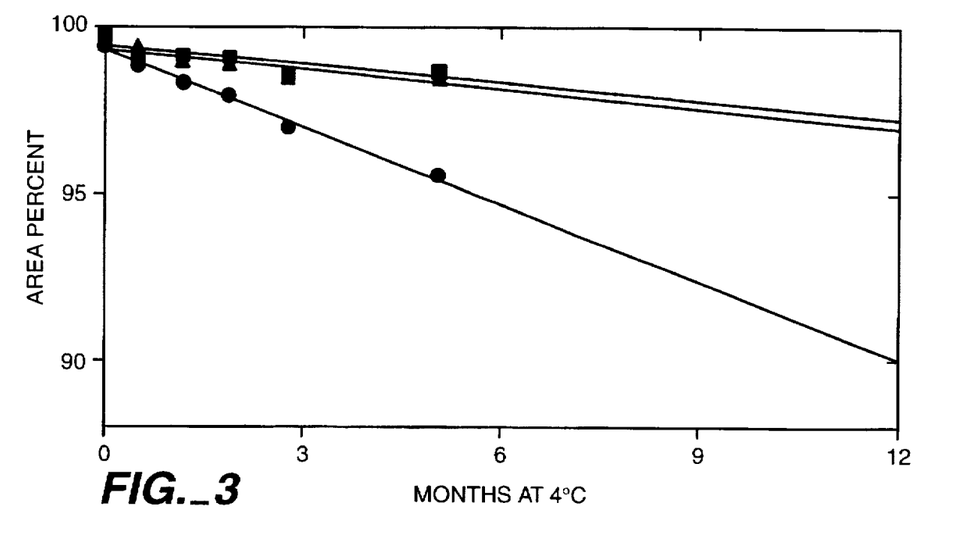
FIG. 3 shows the relative rates of degradation of CRF during storage at 4° C. in liquid formulations wherein the liquid formulations tested are 1 mg/ml CRF, pH 4.0, 20 mM acetate ("●"), 1 mg/ml CRF, pH 4.0, 20 mM acetate, 5% mannitol ("■") and 1 mg/ml CRF, pH 4.0, 20 mM acetate, 5% sorbitol ("▲").

The results of the studies performed at 4° C. are presented in FIG. 3. Specifically, the data presented in FIG. 3 indicate that both the mannitol-containing and sorbitol-containing formulations were significantly more stable than the formulation lacking any additive alcohol at the 2-month, 3-month and 5-month timepoints. These results, therefore, demonstrate that the addition of an alcohol such as mannitol or sorbitol to liquid formulations of CRF functions to provide protection against degradation of CRF when stored as a liquid at 4° C.

EXAMPLE 6

Studies on the Stability of CRF During Storage

Figure 4:
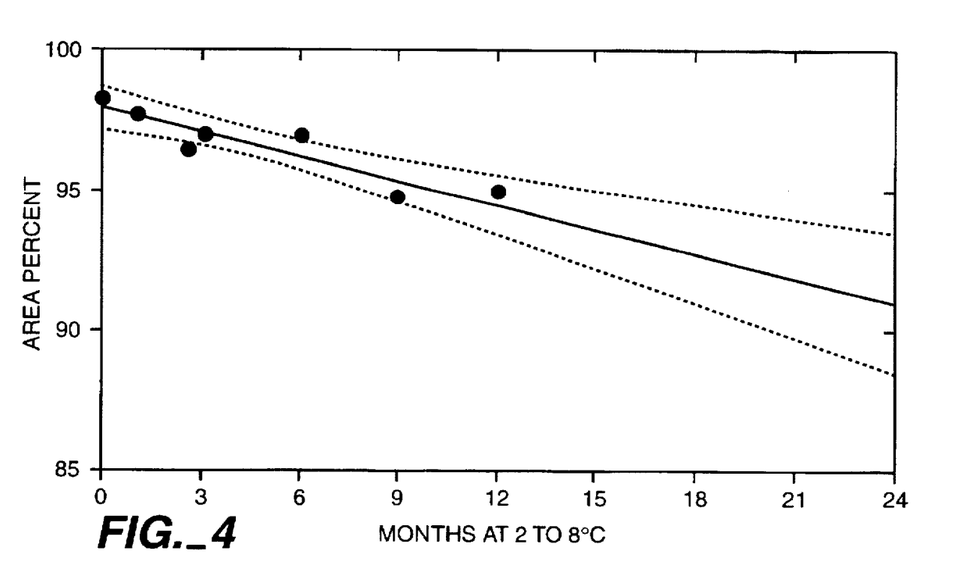
FIG. 4 shows the relative rate of degradation of the CRF peptide in batch number NT194004 when stored at 2° C. to 8° C. over time.
Figure 5:
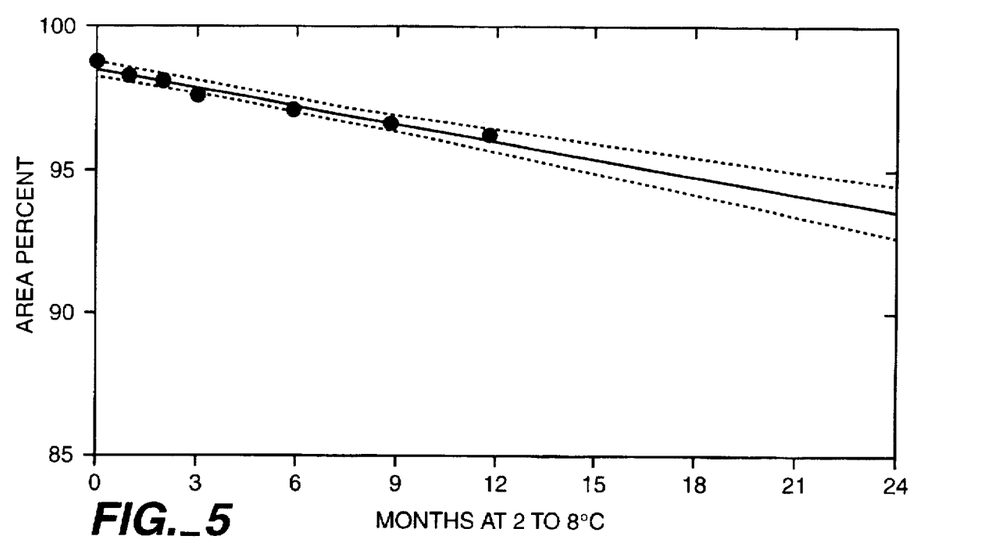
FIG. 5 shows the relative rate of degradation of the CRF peptide in batch number NT195004 when stored at 2° C. to 8° C. over time.

Independent batches of pH 4.0 liquid formulations containing 1 mg/ml CRF in 20 mM acetate buffer and 5% mannitol (batch numbers NT194004 and NT195004), of a pH 7.4 liquid formulation of 1 mg/ml CRF in 10 mM phosphate buffer and 5% mannitol (batch number 17210394) and of a pH 7.4 liquid formulation of 0.5 mg/ml CRF in 10 mM phosphate buffer and 5% mannitol (batch number 29210694) were prepared and were examined for their stability after storage for various periods of time at 2°–8° C. Percent stability of the liquid formulations was measured by subjecting the samples to HPLC analysis after storage for the desired period of time and determining the relative area under the peak corresponding to CRF as compared to the total area under all peaks detected. The results presented in Table 4 and FIGS. 4 and 5 indicate that liquid formulations of CRF in both acetate and phosphate buffers are relatively stable over extended periods of time at 2°–8° C.

TABLE 4

Stability of CRF in Acetate and Phosphate-Based Buffers

| Formulation/Batch Number | Last Timepoint | Percent Stability |
|---|---|---|
| Acetate/NTI94004 | 12 months | 95% |
| Acetate/NTI95004 | 12 months | 96% |
| Phosphate/17210394 | 12 months | 85% |
| Phosphate/29210694 | 15 months | ≧95% |

Two independent batches of CRF-containing formulations (batches NTI-02-03191 and NTI-07-05122) were prepared, lyophilized, stored for varying periods of time at −20° C. to −15° C., reconstituted in saline and tested for their percent stability after storage. Prior to lyophilization, the liquid formulations constituted 0.2 mg/ml CRF, 0.1% HCl and 10 mg/ml mannitol. After 3 years of storage in a lyophilized form at −20° C. to −15° C., batch NTI-02-03191 was shown to be greater than 97% stable by HPLC analysis as described above. After 3-years of storage at −20° C. to −15° C., batch NTI-07-05122 was shown to be greater than 95% stable by HPLC analysis as described above.

EXAMPLE 7

Studies on Pharmaceutical Formulations

A series of studies were carried out to evaluate the effects of different materials on the stability over time of the CRF peptide in various different liquid formulations. Multiple independent sets of CRF liquid formulations were analyzed separately. In each set of liquid formulations, an initial pH 4.0 liquid formulation consisting of 1 mg/ml CRF in 20 mM acetate buffer and 5% mannitol ("control" formulation) was employed and various components were either added thereto ("added" in Table 5), or in some cases, were substituted for a certain component or components in the initial formulation ("sub for . . . " in Table 5). Each formulation in each set of formulations was then stored at 40° C. and the degree of degradation of the CRF peptide was determined at various timepoints by HPLC analysis. Each separate set of formulations was run with a concurrent control liquid formulation.

The results of these experiments are presented in Table 5. The quantitative results shown in Table 5 are the results obtained from the most recent timepoint of each experiment wherein the final timepoints for each of Sets A–H varied from days to more than eight weeks. Both the assay and purity results are presented as percent relative to the concurrent control; assay is measured as CRF concentration against a reference standard and purity is measured as the purity of the CRF HPLC peak relative to that of the other detectable CRF-related peaks in the sample.

TABLE 5

Stability of CRF in Various Liquid Formulations at 40° C.

| Modification | Concentration | Assay - end of study % of control | Purity - end of study % of control |
|---|---|---|---|
| Set A | | | |
| METHANOL (sub for mannitol) | 1M | 99% | 100% |
| EDTA (added) | 0.05% | 84% | 97% |

TABLE 5-continued

Stability of CRF in Various Liquid Formulations at 40° C.

| Modification | Concentration | Assay - end of study % of control | Purity - end of study % of control |
|---|---|---|---|
| SUCROSE (sub for mannitol) | 5% | 27% | 70% |
| GLYCEROL (sub for mannitol) | 5% | 87% | 98% |
| HISTIDINE (added) | 16 mM | 64% | 74% |
| GLUTAMIC ACID (added) | 12 mM | 95% | 97% |
| Set B | | | |
| MANNITOL (sub for mannitol) | 1% | 106% | 99% |
| MANNITOL (sub for mannitol) | 10% | 105% | 100% |
| SODIUM CHLORIDE (added) | 1% | na | na |
| ACETATE (sub for acetate) | 5 mM | 108% | 100% |
| ACETATE (sub for acetate) | 50 mM | 102% | 99% |
| SUCCINATE (sub for acetate) | 20 mM | 106% | 98% |
| CYSTEINE (added) | 8 mM | 74% | 76% |
| METHIONINE (added) | 11 mM | 107% | 100% |
| ARGININE (added) | 10 mM | 112% | 100% |
| LYSINE (added) | 10 mM | 102% | 99% |
| ZINC ACETATE (added) | 1 mM | 94% | 97% |
| CUPROUS CHLORIDE (added) | 0.9 mM | 8% | 36% |
| FERROUS CHLORIDE (added) | 0.8 mM | 87% | 100% |
| SET C | | | |
| EDTA (added) | 1.2 mM | 70% | 79% |
| METHIONINE (added) | 9.8 mM | 115% | 104% |
| ARGININE (added) | 8.5 mM | 109% | 102% |
| LYSINE (added) | 9.9 mM | 108% | 101% |
| GLUTAMIC ACID (added) | 11 mM | 111% | 101% |
| Set D | | | |
| SODIUM BISULFITE (added) | 4.5 mM | na | na |
| MAGNESIUM CHLORIDE (added) | 1.2 mM | 100% | 99% |
| BHT (added) | 0.1 mM | 93% | 99% |
| PEG (added) | 6.80% | 102% | 95% |
| Set E | | | |
| GLUTAMIC ACID (added) | 50 mM | 88% | 97% |
| GLUTAMIC ACID (added) | 10 mM | 88% | 102% |
| GLUTAMIC ACID (added) | 2 mM | 90% | 103% |
| METHIONINE (added) | 50 mM | 99% | 105% |
| METHIONINE (added) | 10 mM | 99% | 103% |
| METHIONINE (added) | 2 mM | 99% | 102% |
| GLU + MET (added) | 10 + 10 mM | 93% | 102% |
| Set F | | | |
| FERRIC CHLORIDE (added) | 1 mM | 58% | 103% |
| FERRIC CHLORIDE (added) | 0.2 mM | 86% | 102% |
| FERRIC CHLORIDE (added) | 0.05 mM | 92% | 101% |
| CUPRIC CHLORIDE(added) | 1 mM | 91% | 100% |
| CUPRIC CHLORIDE(added) | 0.2 mM | 94% | 101% |
| CUPRIC CHLORIDE (added) | 0.05 mM | 94% | 99% |
| Set G | | | |
| CUPROUS CHLORIDE (added) | 1 mM | 35% | 78% |
| CUPROUS CHLORIDE (added) | 0.2 mM | 71% | 93% |
| CUPROUS CHLORIDE (added) | 0.05 mM | 91% | 98% |
| Set H | | | |
| METHIONINE (added) | 10 mM | 109% | 101% |
| METHIONINE (added) | 50 mM | 110% | 102% |
| ACETATE (sub for acetate) | 10 mM | 91% | 99% |
| ACETATE (sub for acetate) | 5 mM | 84% | 91% |
| METHIONINE ONLY | 20 mM | 126% | 105% |
| Set I | | | |
| pH 7.4 10 mM PO$_4$/5% mannitol | | na | 95% |
| pH 7.4 10 mM PO$_4$/5% mannitol | 10 mM Glu | na | 86% |
| pH 7.4 10 mM PO$_4$/5% mannitol | 10 mM Met | na | 98% | na = not available

The results presented in Table 5 demonstrate that the addition of amino acids such as methionine, arginine, lysine and glutamic acid provides protection against degradation of the CRF peptide in a liquid formulation. It is believed that the free amino acids alter the mechanism and rate of degradation of the peptide. In the case of additive methionine, the amino acid acts as a substitute site for oxidation, thereby reducing the oxidation of CRF itself. Thus, additive methionine exhibits a protective effect on the CRF peptide.

Furthermore, addition of the potential stabilizers magnesium, cupric or zinc salts also may provide a stabilizing effect against degradation of CRF in a liquid formulation, where as the addition of cuprous chloride appears to have a detrimental effect on CRF stability.

The results presented in Table 5 also indicate that various alcohols such as methanol or glycerol can effectively substitute for mannitol in the liquid formulation without having any significant detrimental effect on stability of CRF and, furthermore, mannitol concentrations in the liquid formulation can be varied between 1% and 10% without having any significant detrimental effect. Moreover, the results presented in Table 5 demonstrate that use of methionine or a succinate-based buffer in place of the control acetate-based buffer has no significant detrimental effect on CRF stability in a liquid formulation.

Finally, the results presented in Table 5 demonstrate that addition of an antioxidant compound such as butylated hydroxytoluene (BHT) has no significant detrimental effects on the stability of CRF in a liquid formulation.

EXAMPLE 8

Studies to Determine the Effects of Additive Methionine on CRF Stability

Figure 6:
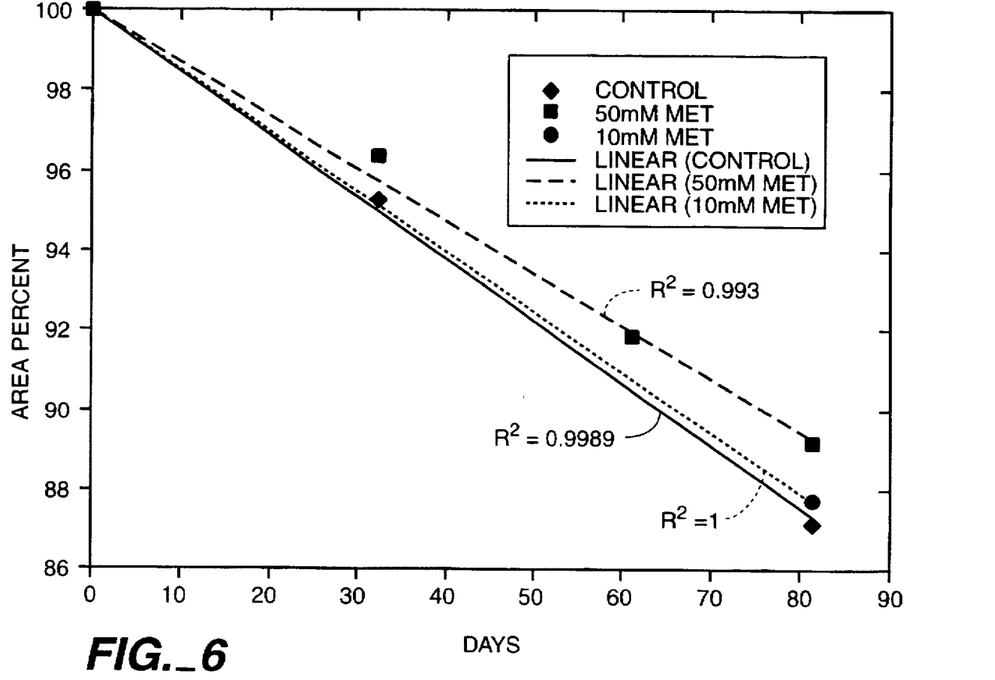
FIG. 6 shows the relative rate of degradation of the CRF peptide at 40° C. in the following liquid formulations over time: 1 mg/ml CRF in 20 mM acetate and 5% mannitol (control) (________), control plus 10 mM methionine ( . . . ) and control plus 50 mM methionine (— — — — —).

Follow-up experiments were performed to confirm the protective effect provided by the addition of methionine to the CRF formulations of the present invention. FIG. 6 shows the relative rate of degradation of the CRF peptide during storage at 40° C. in a control liquid formulation (20 mM acetate and 5% mannitol) versus that wherein either 10 mM or 50 mM methionine is added to the control formulation. The "area %" of the liquid formulations was measured by subjecting the samples to HPLC analysis after storage for the desired period of time and determining the relative area under the peak corresponding to CRF as compared to the total area under all peaks detected.

The results presented in FIG. 6 demonstrate that while the addition of 10 mM methionine to the CRF formulations provides for a small protective effect against degradation of the peptide at 40° C., addition of 50 mM methionine to the control formulation provides a significantly increased protective effect.

Figure 7:
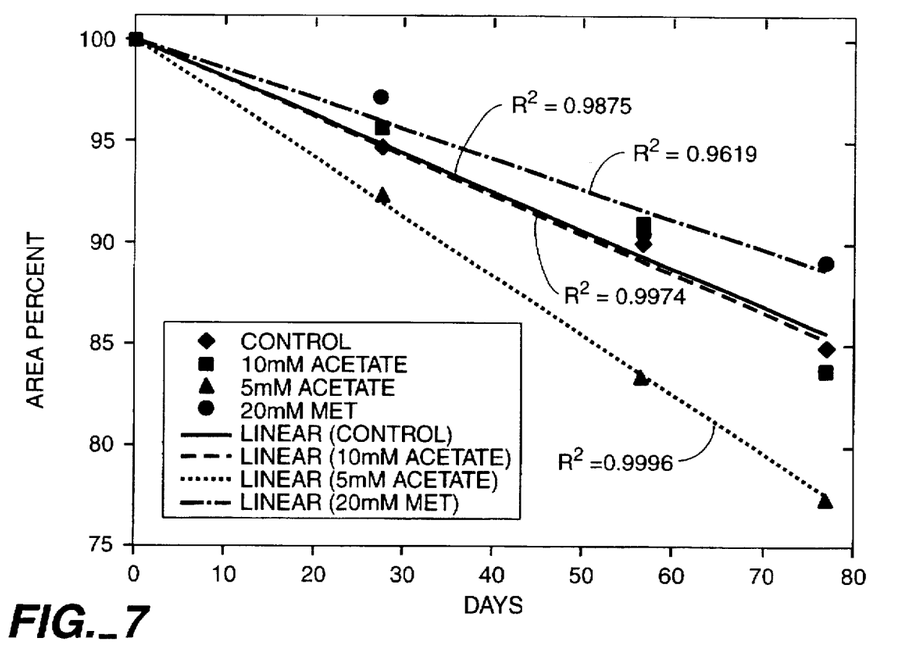
FIG. 7 shows the relative rate of degradation of the CRF peptide at 40° C. in the following liquid formulations over time: 1 mg/ml CRF in 20 mM acetate and 5% mannitol (control) (________), 1 mg/ml CRF in 10 mM acetate and 5% mannitol (— — — — —), 1 mg/ml CRF in 5 mM acetate and 5% mannitol ( . . . ) and 20 mM methionine and 5% mannitol (—. —. —. —. —).

FIG. 7 shows the stability of CRF at 40° C. in the presence of various acetate and/or methionine concentrations. The results presented in FIG. 7 demonstrate that the substitution of 20 mM methionine in place of acetate provides a significant protective effect as compared to that control formulation.

Figure 8:
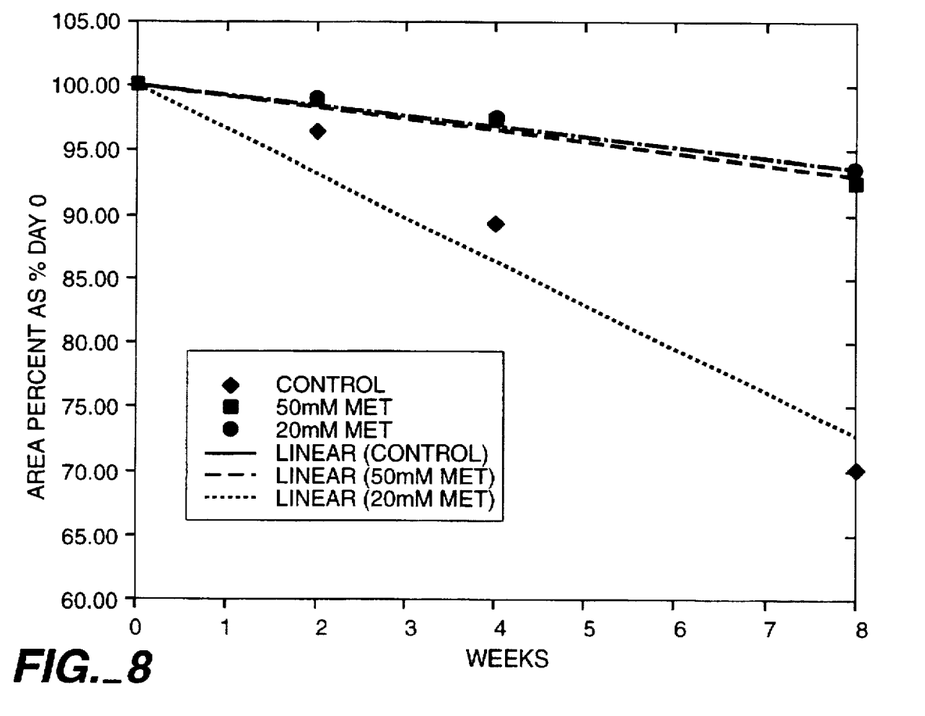
FIG. 8 shows the relative rate of degradation of the CRF peptide at 40° C. in the following liquid formulations over time: 1 mg/ml CRF, pH 4.0 in 20 mM acetate with 5% mannitol (control) (________), 20 mM methionine with 5% mannitol ( . . . ) and 50 mM methionine with 5% mannitol (— — — — —)

Finally, FIG. 8 also demonstrates that the substitution of either 20 mM or 50 mM methionine in place of acetate in formulations of the CRF peptide at 40° C. acts to significantly decrease the rate at which the CRF peptide is degraded.

EXAMPLE 9

Studies to Determine the Stability of CRF as a Lyophilized Powder Versus as a Reconstituted Liquid Experiments were performed to determine the difference in CRF stability when stored as a lyophilized power ("powder" form) versus when stored in a liquid formulation that has been reconstituted from that lyophilized powder ("liquid" form). For these experiments, two different CRF formulations were prepared as lyophilized powders and a portion of each was reconstituted as a liquid. Both the powder and liquid forms of the peptide were then stored over a period of 6 weeks at either 30° C. or 40° C. to determine the amount of CRF degradation that occurred during the storage period. The formulations tested were (1) 0.2 mg/ml CRF in 10 mM succinate, pH 4.0 and 5% mannitol ("succinate" formulation) and (2) 0.2 mg/ml CRF in 10 mM phosphate buffer, pH 7.4 and 5% mannitol ("phosphate" formulation). The results of these experiments are presented in Table 6. The numbers presented in Table 6 represent the % of the initial CRF concentration at each timepoint analyzed. "ND" means that concentration measurements were not performed at those timepoints.

TABLE 6

Stability of Various Liquid and Powder Formulations of CRF

| Formulation/ Form | Temp | CRF concentration (% of initial) | | | | | |
|---|---|---|---|---|---|---|---|
| | | 0 days | 4 days | 7 days | 14 days | 4 wks | 6 wks |
| Succinate/ Powder | 30° C. | 100 | ND | ND | 83 | 101 | 75 |
| Succinate/ Powder | 40° C. | 100 | ND | ND | 63 | 59 | 32 |
| Phosphate/ Powder | 30° C. | 100 | ND | ND | 90 | 103 | 76 |
| Phosphate/ Powder | 40° C. | 100 | ND | ND | 58 | 32 | 66 |
| Succinate/ Liquid | 30° C. | 100 | 92 | 93 | 100 | 121 | ND |
| Phosphate/ Liquid | 30° C. | 100 | 91 | 98 | 92 | 107 | ND |

The data presented in Table 6 indicate that liquid solutions of CRF seem to be as stable over time as the lyophilized powders of CRF. These data are surprising in light of the general acceptance in the art that lyophilized formulations are more stable over time than are their liquid counterparts.

EXAMPLE 10

Subcutaneous and Intracutaneous Irritation Screening

Experiments were performed to determine the irritation potential of various formulations which either possess or lack the CRF peptide. First, two CRF-containing formulations were prepared and administered subcutaneously as a single dose to rats and the degree of irritation at the administration site was observed at various timepoints following administration. The irritation potential of the following formulations was analyzed:

1 mg/ml CRF, pH 4.0, 20 mM acetate buffer, 5% mannitol 1 mg/ml CRF, pH 4.0, 20 mM acetate buffer, 5% sorbitol The results of these experiments demonstrated that both of the formulations analyzed were non-irritating to the test animals when administered as a single dose subcutaneously. When administered subcutaneously daily for seven days to rats, no irritation was observed visually but the formulations demonstrated irritation potential upon microscopic examination of the injection site.

Next, the irritation potential of various liquid vehicles lacking additive CRF was examined in a rabbit intracutaneous irritation model. In this model, the backs of test rabbits are shaved. 0.2 ml of each test formulation vehicle is injected intracutaneously at five different sites on the back of the rabbit and the injection sites are observed for the presence of erythema/eschar formation and edema at 24, 48 and 72 hours after injection. At each observational time point, erythema/eschar formation is scored on a scale of 0 to 4 as shown in Table 7.

TABLE 7

Scoring of Erythema and Eschar Formation

| | Score |
|---|---|
| No erythema | 0 |
| Very slight erythema (barely perceptible) | 1 |
| Well-defined erythema | 2 |
| Moderate to severe erythema | 3 |
| Severe erythema (beet-redness) to slight eschar formation | 4 |

Furthermore, at each observational time point, edema formation, excluding non-inflammatory (mechanical) edema from the blank or extraction fluid, is scored on a scale of 0 to 4 as shown in Table 8.

TABLE 8

Scoring of Edema Formation

| | Score |
|---|---|
| No edema | 0 |
| Very slight edema (barely perceptible) | 1 |
| Light edema (edges of area well defined by definite raising) | 2 |
| Moderate edema (raised about 1 mm) | 3 |
| Severe edema (raised more than 1 mm and extending beyond area of exposure | 4 |

Upon completion of the studies, a "mean irritation score" is determined for each formulation tested by adding the erythema/eschar formation score and the edema score at each of the five injection sites and at each of the three different observational time points and dividing that total score by the number of scores taken at each site and at each observational time point (2) multiplied by the number of injection sites observed at each time point (5) multiplied by the number of observational time points (3). The mean irritation scores of various different CRF formulation vehicles are shown in Table 9.

TABLE 9

Mean Irritation Scores for Various CRF Vehicle Solutions

| Test Vehicle | Mean irritation score |
|---|---|
| Saline control | 0 |
| pH 4.0, 20 mM NaOAc buffer | 2.9 |
| pH 4.0, 20 mM NaOAc buffer, 5% mannitol | 0.8 |
| pH 4.0, 5 mM NaOAc buffer, 5% mannitol | 0 |
| pH 7.4, 10 mM PO$_4$ buffer | 0.6 |
| pH 7.4, 10 mM PO$_4$ buffer, 5% mannitol | 0 |

These results demonstrate that while the pH 4.0, 20 mM acetate buffer vehicle exhibits a relatively high mean irritation score, addition of an alcohol such as mannitol to that vehicle has the effect of significantly reducing the irritative effect of the liquid formulation. The same protective effect is observed when mannitol is employed in association with a phosphate buffer at pH 7.4.

Similar experiments were performed to determine the effects of additive methionine on the irritation potential of a CRF formulation. The results of the experiments testing various different formulation vehicles are shown in Table 10.

TABLE 10

Mean Irritation Scores for Various CRF Vehicle Solutions

| Test Vehicle | Mean irritation score |
|---|---|
| Saline control | 0 |
| pH 4.0, 20 mM NaOAc buffer, 5% mannitol | 2.3 |
| pH 4.0, 10 mM NaOAc buffer, 5% mannitol | 0.8 |
| pH 4.0 5 mM NaOAc buffer, 5% mannitol | 0.3 |
| pH 4.0, 5 mM NaOAc buffer, 5% mannitol, 20 mM methionine | 0.6 |
| pH 4.0, 5 mM NaOAc buffer, 5% mannitol, 50 mM methionine | 0 |
| pH 4.0, 20 mM methionine, 5% mannitol | 0 |
| pH 4.0, 50 mM methionine, 5% mannitol | 0 |

The results presented in Table 10 demonstrate that methionine-containing formulations are generally less irritating than similar formulations lacking methionine. Also, substitution of methionine for acetate results in a formulation which is less irritating.

The foregoing description of the preferred embodiments of the present invention has been presented for purposes of illustration and description. They are not intended to be exhaustive or to limit the invention to the precise form disclosed, and many modifications and variations are possible in light of the above teaching. Such modifications and variations which may be apparent to a person skilled in the art are intended to be within the scope of the invention.

What is claimed is:

1. A pharmaceutically acceptable formulation of corticotropin releasing factor (CRF) comprising (a) a pharmaceutically effective amount of CRF, (b) a buffer at a concentration of from about 1 mM to about 50 mM which functions to maintain the pH of said formulation between about 2.0 to about 5.0 or between about 6.0 to about 9.0 when said formulation is in liquid form, wherein the anion of said buffer is selected from the group consisting of acetate, phosphate, carbonate, succinate, citrate, borate, tartrate, fumarate and lactate and (c) an alcohol, in a concentration of from about 1% to about 10%, wherein said alcohol is selected from the group consisting of mannitol, sorbitol, ribotol, arabitol, xylitol, inositol, galactitol, methanol, ethanol and glycerol.

2. The formulation according to claim 1 further comprising an amino acid selected from the group consisting of methionine, arginine, lysine, cysteine, glutathione and glutamic acid in a concentration from about 1 mM to about 100 mM.

3. The formulation according to claim 2 wherein the amino acid is methionine.

4. The formulation according to claim 3 wherein said methionine is at a concentration from about 10 mM to about 50 mM.

5. The formulation according to claim 1 further comprising a sugar in a concentration from about 1% to about 10%.

6. The formulation according to claim 5 wherein the sugar is selected from the group consisting of glucose, sucrose, lactose, fructose, trehalose and mannose.

7. The formulation according to claim 1 further comprising a ferric or cupric salt in a concentration from about 0.05 mM to about 1 mM.

8. The formulation according to claim 7 wherein said ferric or cupric salt is ferric chloride or cupric chloride.

9. The formulation according to claim 1 further comprising butylated hydroxytoluene in a concentration from about 0.05 mM to about 0.5 mM.

10. The formulation according to claim 1 further comprising magnesium chloride or zinc chloride in a concentration from about 0.5 mM to 2.0 mM.

11. The formulation according to claim 1 further comprising any chemically compatible preservative.

12. The formulation according to claim 11 wherein said chemically compatible preservative is selected from the group consisting of benzyl alcohol, chlorobutanol, phenol, cresol, methyl paraben and propyl paraben.

13. The formulation according to claim 1 wherein said formulation is 0.5–3 mg/ml CRF in 20 mM acetate buffer and 5% mannitol at pH 4.0.

14. The formulation according to claim 1 wherein said formulation is 0.5–3 mg/ml CRF in 20 mM acetate buffer, 5% mannitol and 50 mM methionine at pH 4.0.

15. A pharmaceutically acceptable formulation of corticotropin releasing factor (CRF) comprising (a) a pharmaceutically effective amount of CRF, (b) an amino acid at a concentration of from about 1 mM to about 100 mM, wherein said amino acid is selected from the group consisting of methionine, arginine, lysine, cysteine, glutathione and glutamic acid and (c) an alcohol, in a concentration of from about 1% to about 10%, wherein said alcohol is selected from the group consisting of mannitol, sorbitol, ribotol, arabitol, xylitol, inositol, galactitol, methanol, ethanol and glycerol.

16. The formulation according to claim 15 wherein said amino acid is methionine.

17. The formulation according to claim 16 wherein said methionine is present at a concentration of from about 10 mM to about 50 mM.

18. The formulation according to claim 17 wherein said methionine is present at a concentration of about 20 mM.

19. The formulation according to claim 15 wherein said formulation is 0.5–3 mg/ml CRF in 20 mM methionine and 5% mannitol at pH 4.0.

20. The formulation according to claim 15 further comprising a chemically compatible preservative.

21. The formulation according to claim 20 wherein said chemically compatible preservative is selected from the group consisting of benzyl alcohol, chlorobutanol, phenol, cresol, methyl paraben and propyl paraben.

22. The formulation according to claims 1 or 15 in liquid form.

23. The formulation according to claims 1 or 15 in lyophilized form.

24. A method of preparing a pharmaceutically acceptable formulation of corticotropin releasing factor peptide comprising dissolving said corticotropin releasing factor peptide in a solution comprising (a) either (i) a buffer at a concentration of from about 1 mM to about 50 mM which functions to maintain the pH of said formulation between about 2.0 to about 5.0 or between about 6.0 to about 9.0 when said formulation is in liquid form, wherein the anion of said buffer is selected from the group consisting of acetate, phosphate, carbonate, succinate, citrate, borate, tartrate, fumarate and lactate or (ii) an amino acid at a concentration of from about 1 mM to about 100 mM, wherein said amino acid is selected from the group consisting of methionine, arginine, lysine, cysteine, glutathione and glutamic acid and (b) an alcohol in a concentration of from about 1% to about 10%, herein said alcohol is selected from the group consisting of mannitol, sorbitol, ribotol, arabitol, xylitol, inositol, galactitol, methanol, ethanol and glycerol.

25. The method according to claim 24 wherein when said solution comprises said buffer, the further step of adding to said formulation an amino acid selected from the group consisting of methionine, arginine, lysine, cysteine, glutathione and glutamic acid in a concentration from about 1 mM to about 100 mM.

26. The method according to claim 24 further comprising the step of adding to said formulation a sugar in a concentration from about 1% to about 10%.

27. The method according to claim 26 wherein the sugar is selected from the group consisting of glucose, sucrose, lactose, fructose, trehalose and mannose.

28. The method according to claim 24 further comprising the step of adding to said formulation a ferric or cupric salt in a concentration from about 0.05 mM to about 1 mM.

29. The method according to claim 28 wherein said ferric or cupric salt is ferric chloride or cupric chloride.

30. The method according to claim 24 further comprising the step of adding to said formulation butylated hydroxytoluene in a concentration from about 0.05 mM to about 0.5 mM.

31. The method according to claim 24 further comprising the step of adding to said formulation magnesium chloride or zinc chloride in a concentration from about 0.5 mM to 2.0 mM.

32. The method according to claim 24 further comprising adding a chemically compatible preservative.

33. The method according to claim 32 wherein said chemically compatible preservative is selected from the group consisting of benzyl alcohol, chlorobutanol, phenol, cresol, methyl paraben and propyl paraben.

34. The method according to claim 24 further comprising the step of introducing said formulation into its storage container under inert gas.

35. The method according to claim 24 further comprising the step of lyophilizing said formulation.

36. A method for enhancing the stability of corticotropin releasing factor in a formulation thereof comprising adding to said formulation an amino acid selected from the group consisting of methionine, arginine, lysine, cysteine, glutathione and glutamic acid in a concentration from about 1 mM to about 100 mM.

37. The method according to claim 36 wherein said amino acid is methionine.

38. A method for reducing inflammation or edema in a mammal, said method comprising administering to said mammal a therapeutically effective amount of the formulation according to claims 1 or 15.

39. The method according to claim 38 wherein said formulation is administered by the intravenous, subcutaneous, intramuscular, nasal or pulmonary routes of administration.

* * * * *